United States Patent [19]
Kaneko et al.

[11] Patent Number: 5,410,473
[45] Date of Patent: Apr. 25, 1995

[54] METHOD AND APPARATUS FOR RECORDING ELECTROCARDIOGRAM INFORMATION

[75] Inventors: Mutsuo Kaneko; Yumi Nishimura; Noriko Igarashi; Minako Sakai; Akihiro Motoki, all of Tokyo, Japan

[73] Assignee: Fukuda Denshi Kabushiki Kaisha, Japan

[21] Appl. No.: 991,873

[22] Filed: Dec. 16, 1992

[30] Foreign Application Priority Data

Jan. 7, 1992 [JP] Japan .................................. 4-000687

[51] Int. Cl.⁶ .......................... G06F 15/42; A61B 5/04
[52] U.S. Cl. ............................ 364/413.06; 364/413.02; 364/413.04; 364/413.05; 128/696; 128/697
[58] Field of Search .................... 364/413.06, 413.02, 364/413.04, 413.05; 128/696, 697

[56] References Cited

U.S. PATENT DOCUMENTS

| | | | |
|---|---|---|---|
| 3,874,370 | 4/1975 | Harris et al. | 126/2.6 A |
| 3,909,792 | 9/1975 | Harris et al. | 340/172.5 |
| 3,940,692 | 2/1976 | Neilson | 324/77 R |
| 4,098,267 | 7/1978 | Stein et al. | 128/2.06 G |
| 4,537,202 | 8/1985 | Mancini | 128/712 |
| 4,896,677 | 1/1990 | Kaneko et al. | 128/696 |
| 5,058,597 | 10/1991 | Onada et al. | 128/696 |
| 5,092,343 | 3/1992 | Spitzer et al. | 128/733 |

FOREIGN PATENT DOCUMENTS 1-170440A 5/1989 Japan .
2-63008 12/1990 Japan .
2214309 8/1989 United Kingdom .

OTHER PUBLICATIONS

Analysis of Ambulatory ECG By Superimposed Waveforms and (ECG) Wave Trendgram, Japan Soc. ME & BE (May, 1989), by M. Kaneko et al., p. 286 (including an English translation).
Development and Application of the Evaluation Method of Ischemic ECG Change by the Superimposing Processing, J. Electrocardiology, vol. 11, No. 4, 1991, by Masatoshi Hari, pp. 396–407.

Primary Examiner—Gail O. Hayes
Assistant Examiner—Gita D. Shingala
Attorney, Agent, or Firm—Merchant, Gould, Smith, Edell, Welter & Schmidt

[57] ABSTRACT

A method and apparatus for recording electrocardiogram information, in which ST deviation can readily be visualized and ischemia can be diagnosed with ease at the same time. Compressed recorded waveforms of electrocardiogram waveforms are partitioned and recorded as compressed waveforms of a plurality of lines in a first recording area of a recording paper for recording electrocardiogram information. A predetermined number of lines of the recorded compressed electrocardiogram waveforms in the first recording area are selected in a second recording area neighboring the first recording area, the selected waveforms are superimposed in synchronism with a predetermined characteristic point of the selected waveforms, and the waveforms are recorded while changing location in the area neighboring the predetermined lines of the first recording area. An HR graph and an ST-trend graph of the electrocardiogram waveforms recorded in the first recording area are recorded in recording lines approximately perpendicular to the recording lines of the compressed electrocardiogram waveforms from a position of a recording starting line of the compressed electrocardiogram waveforms of the first recording area.

17 Claims, 12 Drawing Sheets

FIG. 12

METHOD AND APPARATUS FOR RECORDING ELECTROCARDIOGRAM INFORMATION

BACKGROUND OF THE INVENTION

This invention relates to a method and apparatus for recording electrocardiogram information. More particularly, the invention relates to an electrocardiogram information recording method and apparatus through which diagnosis is facilitated, such as diagnosis of ischemia.

Apparatus which continuously record an electrocardiogram for an extended period of time and then subsequently reproduce the recorded waveforms and discriminate a change in the waveforms have recently been developed for the purpose of discovering heart disease and gaining an accurate understanding of the condition of the disease.

These apparatus include some which allow the recording of electrocardiograms to be continued for 24 hours or longer.

In the prior art, these apparatus are adapted to compress the stored electrocardiogram signal and either continuously record or display the compressed electrocardiogram.

A method of recording electrocardiogram information for an extended period of time is disclosed in the specification of Japanese Patent Publication Kokoku Hei 2-63008.

Figure 11:
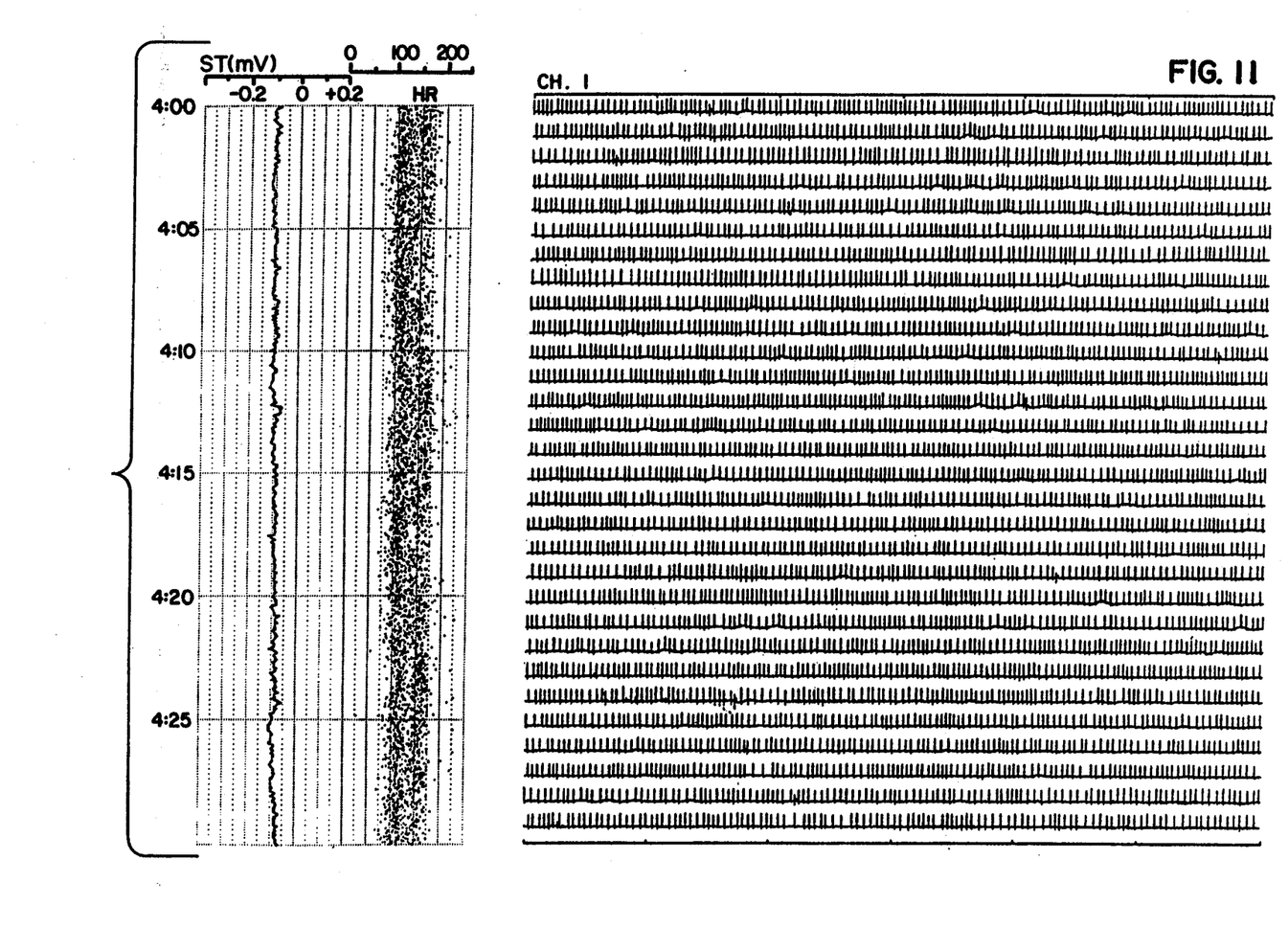
FIGS. 11 and 12 show examples of outputs of electrocardiogram waveforms according to the prior art.

This method involves recording the compressed electrocardiogram waveform on the right side of the recording paper in a portion occupying, say, two-thirds of the page, and recording the ST trend and heart rate (HR), which correspond to the recorded compressed electrocardiogram, on the portion of the recording paper on the left side. FIG. 11 illustrates an example of electrocardiogram information according to this method.

In accordance with this method, the ST trend and the HR are recorded so as to correspond to the compressed electrocardiogram. Therefore, if an abnormal point in the ST trend is followed up on the right side, the position of the abnormal electrocardiogram can be determined immediately. This is advantageous in that diagnosis is easy to perform.

Another method is disclosed in the specification of Japanese Patent Application Laid-Open No. 1-170440 (U.S. Pat. No. 4,896,677; GBP 2,214,309; West German Patent Application 3,843,714.7), although this is not necessarily a method solely for the extended recording of electrocardiograms.

Figure 12:
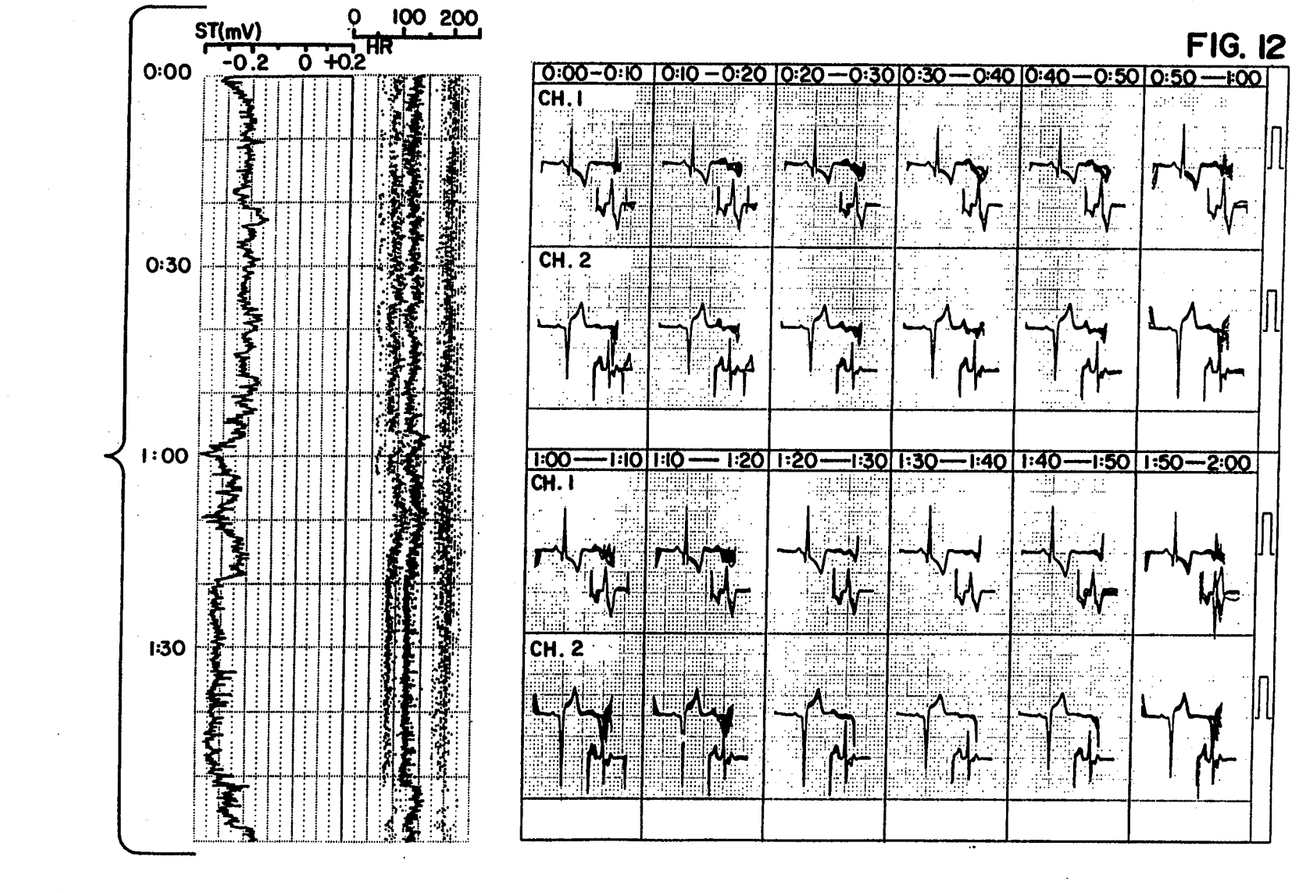

This method involves superimposing electrocardiogram waveforms in synchronism with a prescribed characteristic point in the waveforms, and recording the superimposed waveforms while changing the displayed position in fixed amounts. FIG. 12 illustrates an example of electrocardiogram information according to this method. This method also makes it possible to readily visualize the deviation of ST so that ischemia can be diagnosed witch ease.

In the former method, however, the electrocardiogram waveforms themselves are compressed. As a consequence, the ST in one heartbeat cannot be visualized and the ST deviation cannot be seen. This hinders diagnosis of ischemia.

In the latter method, it is easy to diagnose ischemia since the deviation of the ST can readily be seen. However, the electrocardiogram itself cannot be observed, and therefore the position of an abnormal waveform cannot be determined.

Furthermore, if too many waveforms are superimposed, the ST deviation cannot be observed adequately, and it is required that the displayed position be changed when a certain number of waveforms have been superimposed. Consequently, when it is attempted to record electrocardiogram waveforms over a long period of time, a large recording area also is required. When it is attempted to reduce the recording area, the displayed waveforms must themselves be made small, but this has the effect of detracting from the merits of the method.

SUMMARY OF THE INVENTION

An object of the present invention is to facilitate diagnosis by adopting an arrangement in which the ST trend and compressed electrocardiogram waveforms are displayed simultaneously in mutually correlated form so that the position of an abnormal electrocardiogram can readily be determined by tracing the abnormal location of the ST trend on the right side.

Another object of the present invention is to adopt an arrangement in which uncompressed electrocardiogram waveforms also are displayed simultaneously in correspondence with compressed waveforms so that ST deviation also can be readily visualized, thereby also making it possible to readily diagnose ischemia at the same time.

According to the present invention, the foregoing objects are attained by providing a method and apparatus for recording electrocardiogram information characterized in that compressed recorded waveforms of electrocardiogram waveforms are partitioned and recorded as compressed waveforms of a plurality of lines in a first recording area of a recording paper, results of analyzing the electrocardiogram waveforms recorded in the first recording area are recorded in a recording line approximately perpendicular to the recording lines of the compressed electrocardiogram waveforms from a position of a recording starting line of the compressed electrocardiogram waveforms of the first recording area in a second recording area or third recording area neighboring the first recording area, a predetermined number of electrocardiogram waveforms from among a predetermined number of lines of the recorded compressed electrocardiogram waveforms in the first recording area are selected in whichever of the second and third recording areas the results of analysis are not stored, the selected waveforms are superimposed in synchronism with a predetermined characteristic point of the selected waveforms, and the waveforms are recorded while changing location every predetermined number of lines of the first recording area.

In the arrangement described above, the ST trend and the compressed waveforms are recorded in correlated form, and therefore diagnosis can be performed with ease. Furthermore, since the uncompressed electrocardiogram waveforms also are recorded simultaneously in correlation with the compressed waveforms, the ST deviation can readily be visualized and diagnosis of ischemia also can be performed with ease.

Further objects, features and advantages of the present invention will become apparent from the following detailed description of embodiments of the present invention with reference to the accompanying drawings.

DESCRIPTION OF THE PREFERRED EMBODIMENT

Embodiments according to the present invention will now be described in detail with reference to the drawings.

First Embodiment

Figure 1:
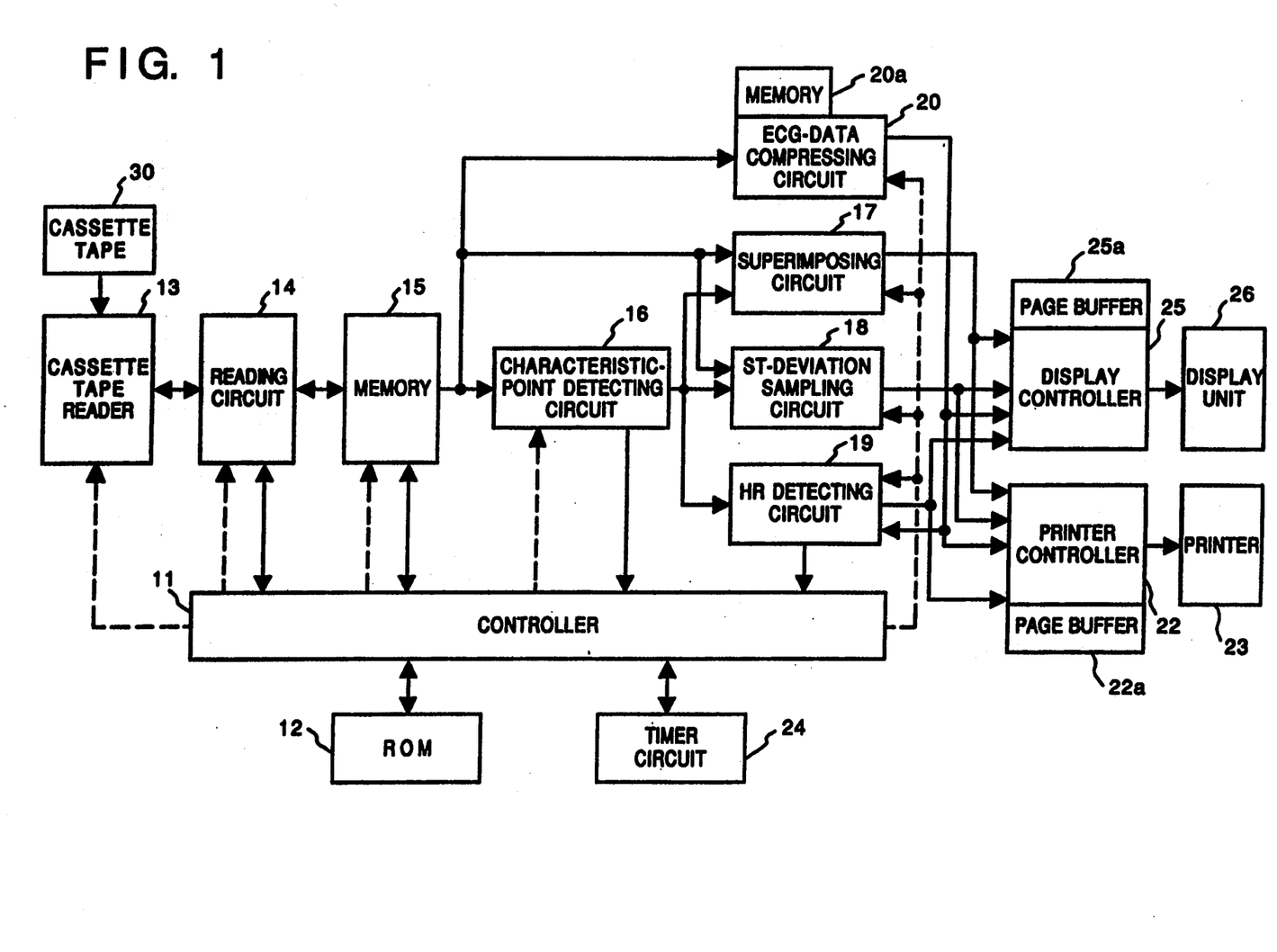
FIG. 1 is a block diagram showing a first embodiment of an electrocardiogram information recording apparatus according to the present invention.

FIG. 1 is a block diagram showing an electrocardiogram recording apparatus according to a first embodiment of the present invention. The apparatus includes a controller 11 for administering control of the overall apparatus in accordance with a program shown in FIGS. 4 through 6 and stored in a ROM 12. The ROM 12 stores various parameters in addition to the above-mentioned program. A cassette tape reader 13 reads electrocardiogram waveforms from a cassette tape 30 on which the electrocardiogram waveforms have been recorded by an electrocardiogram recording. A reading circuit 14 which controls the cassette tape reader 13 reads the electrocardiogram waveforms from the cassette tape 30, binarizes the waveforms and stores the results in a memory 15. The memory 15 is capable of storing at least two beats of electrocardiogram waveforms from the reading circuit 14.

A characteristic-point detecting circuit 16 reads electrocardiogram waveforms from the memory 15 and detects a characteristic point designated by the controller 11. For example, the detecting circuit 16 detects the peak of the R-wave. A superimposing circuit 17 extracts electrocardiogram waveforms from the memory 15 at a predetermined time interval and superimposes a fixed number of these waveforms in synchronism with the characteristic point detected by the detecting circuit 16. In this embodiment, one electrocardiogram waveform is sampled every 30 seconds. When a total of ten sampling waveforms have been extracted and superimposed (ten waveforms are extracted from the electrocardiogram waveforms and superimposed in five minutes), the superimposed waveforms are sent to a printer controller 22 and a display controller 25, whence they are written in predetermined superimposed-waveform storage areas of page buffers 22a, 25a, respectively.

Figure 7:
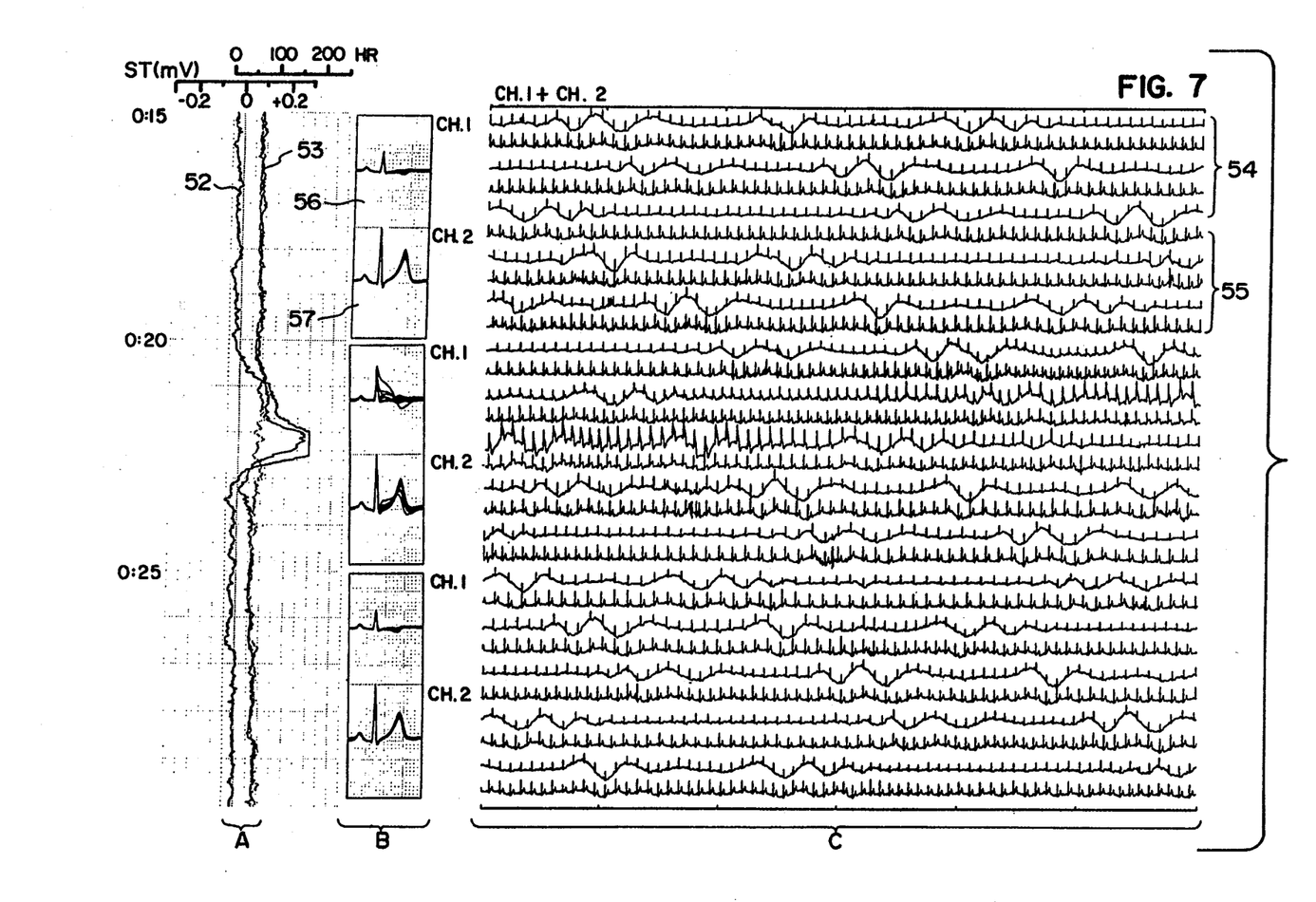
FIG. 7 is a diagram showing an example of output of electrocardiogram waveforms according to this embodiment.
Figure 8:
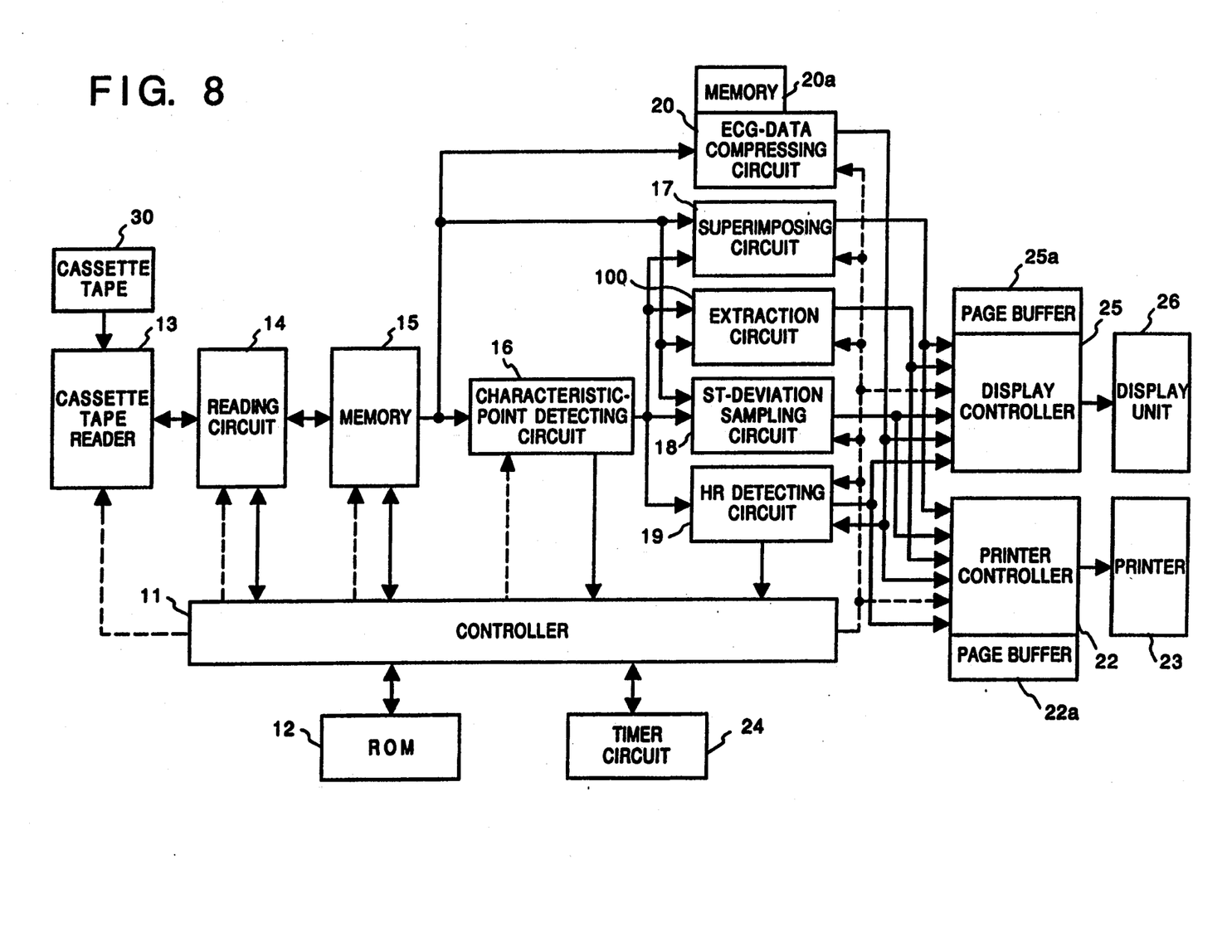
FIG. 8 is a block diagram showing an electrocardiogram information recording apparatus of a third embodiment according to the present invention.

Referring to FIGS. 7 and 8, each of the page buffers 22a and 25a contains three section. Section C contains detailed electrocardiogram data with a time scale in the horizontal direction. Section B contains the same information as Section C but has portions overlaid upon each other at fixed time interval. Section A is the HR and ST value but the time scale is compressed and in the vertical direction. These three sections are written as appropriate data becomes available. When a page of data has been gathered, the page image is sent to the printer which produces a page of printing similar to that shown in FIG. 7.

An ST-deviation sampling circuit 18 samples values of the electrocardiogram waveforms, reads out of the memory 15, at any fixed timing between S and T, and creates an ST trend graph. An HR detecting circuit 19 measures, say, the time interval of the R-wave peaks of the electrocardiogram waveform and detects heart rate (HR). An ECG-waveform compressing circuit 20 shapes the electrocardiogram waveforms, which have been read out of the memory 15, by time compression and writes the compressed waveforms vertically every minute, by way of example. The compressed electrocardiogram waveforms are sent to the printer controller 22 and display controller 25 and are stored in prescribed compressed-waveform storage areas of the page buffers 22a, 25a, respectively.

The printer controller 22 gathers the superimposed electrocardiogram waveforms from the superimposing circuit 17, the ST-trend graph from the ST-deviation sampling circuit 18, HR-trend graph data from the HR detecting circuit 19 and the compressed electrocardiogram waveforms from the ECG-waveform compressing circuit 20, and prints out this information using a printer 23. The printer 23 prints out the waveform information that has been stored in the page buffer 22a.

The display controller 25 gathers the superimposed electrocardiogram waveforms from the superimposing circuit 17, the ST-trend graph from the ST-deviation sampling circuit 18, HR-trend graph data from the HR detecting circuit 19 and the compressed electrocardiogram waveforms from the ECG-waveform compressing circuit 20, and displays this information on the CRT display screen of a display unit 26.

Figure 2:
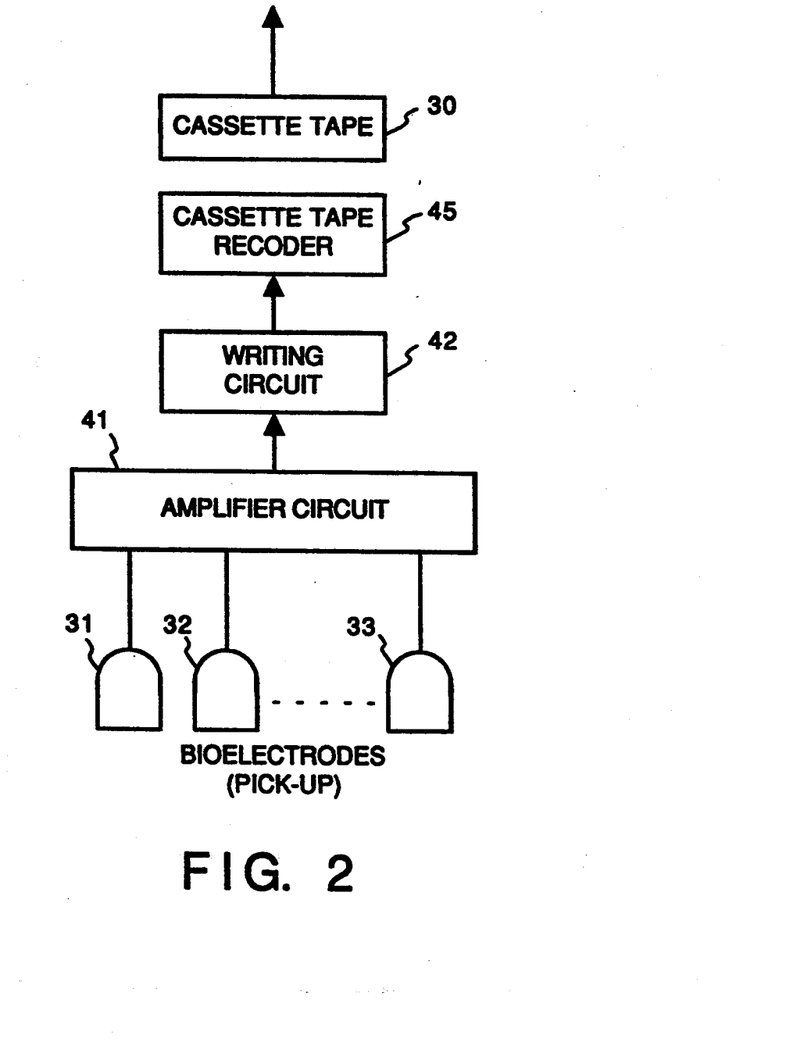
FIG. 2 is a block diagram showing an electrocardiogram recording device which records electrocardiogram waveforms used in this embodiment.

FIG. 2 is a block diagram of an electrocardiogram recorder for storing electrocardiogram waveforms, which have been acquired from a patient, on the cassette tape 30. Biological induction electrodes 31–33 are affixed to the patient for deriving the electrocardiogram waveform. An amplifier circuit 41 amplifies the electrocardiogram waveforms from the electrodes 31–33 and outputs them to a writing circuit 42, which proceeds to record these waveforms on a cassette tape recorder 45.

Figure 3:
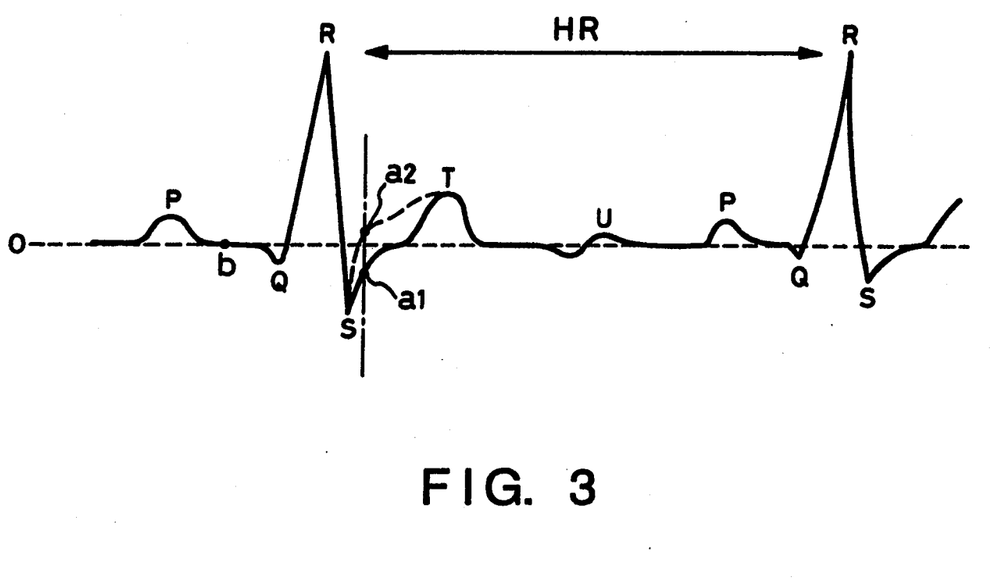
FIG. 3 is a diagram for describing an electrocardiogram waveform.

The electrocardiogram waveforms derived by the biological induction electrodes 31–33 ordinarily are repeating spikes shown in FIG. 3 and the spikes are named P, Q, R, S and T in succession. The P wave is produced by atrial excitation of the heart, the Q, R, S waves are produced by ventricular excitation of the heart, and the T wave is produced by ventricular excitation and relaxation. There are occasions where a small pulse referred to as U wave is produced after the T wave.

Arrhythmia and obstacles to the transmission of excitation are judged from the time relationship of these spikes, and cardiac infarction such as ischemic heart disease, myocarditis and pericarditis, hypertrophy of the left and right auricles and ventricles, electrolytic abnormalities, medicinal effectiveness and endocrinal abnormalities can be diagnosed from changes in the shape of the spikes. In order to perform such diagnosis, it is essential that the state of the change in the waveforms be capable of ready recognition. Since locations at which changes occur are approximately determined by the particular segment of the waveform, the characteristic-point detecting circuit should be adapted so as to detect a characteristic point immediately preceding these segments in order that changes in these segments, which are important in diagnosis, may be recognized with ease.

Deviation of the ST segment is that most often used in diagnosis.

To this end, first of all the crest value at an arbitrary measurement point is measured by the ST-deviation sampling circuit 18 in order to create an ST-trend graph. The sampling circuit 18 samples the crest value, which is a potential difference from a reference point b at a reference level, at a specific point on a specific line, indicated by the dot-and-dash line, that is located a prescribed period of time after the R wave. This sampling is performed in synchronism with the R-wave peak. There are cases in which the specific point is $a_1$ indicated by the solid line in FIG. 3, or $a_2$ indicated by the dashed line. The crest value has a negative value in case of $a_1$ and a positive value in case of $a_2$. These crest values are displayed successively as a trend graph. This trend graph is an ST-trend graph.

Besides the ST-trend graph, in this embodiment, the superimposing circuit 17 extracts one electrocardiogram waveform every predetermined number of such waveforms using the R-wave peak, which is a characteristic point immediately preceding the ST segment, as a synchronizing point, superimposes a predetermined quantity of the extracted electrocardiogram waveforms and outputs them while successively changing the recorded position. This makes it possible to recognize the ST deviation at a glance.

More specifically, as shown in FIG. 7, described below, with the position of the R-wave peak serving as a characteristic point, electrocardiogram waveforms are extracted at a predetermined time interval (e.g., one every 30 second) in synchronization with this characteristic point, a total of ten of these waveforms (the total extracted in five minutes) are superimposed, and these are displayed/outputted, in correlation with the display of the compressed waveforms, together with the recording of the compressed waveforms while the recorded position is changed. As a result, a comparison with the compressed electrocardiogram waveforms can be made concurrent with the output thereof, and superimposed waveforms that are large in size can be displayed/outputted at the same time. In addition, the ST deviation can be recognized at a glance.

Furthermore, the HR graph and the ST trend graph, in which the crest values of the arbitrary positions of the ST segments are recorded, can be gathered together and displayed/outputted simultaneously at the same time as the superimposed waveforms, thereby making it possible to readily recognize a number of electrocardiogram waveform deviations.

Figure 5:
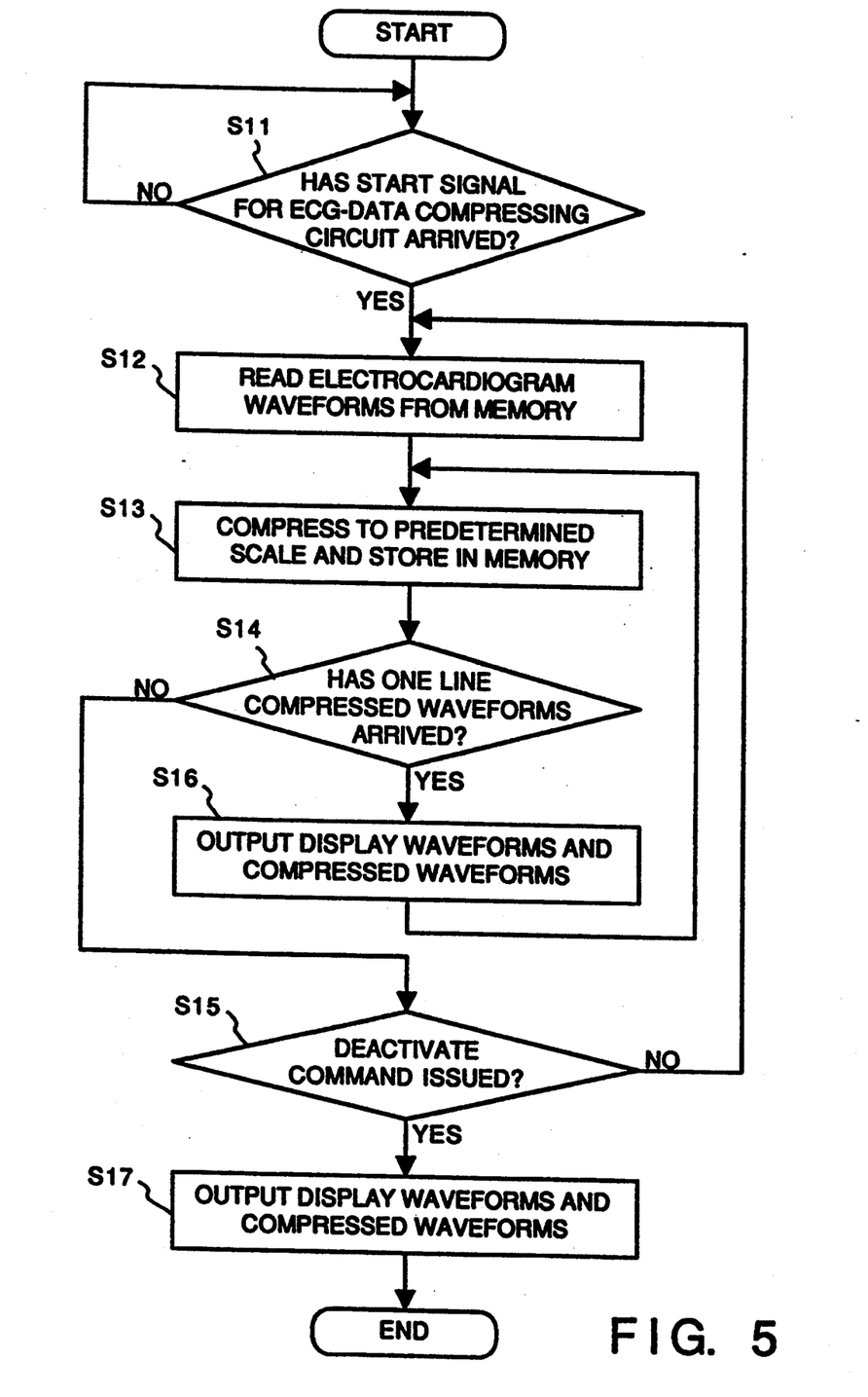
Figure 6:
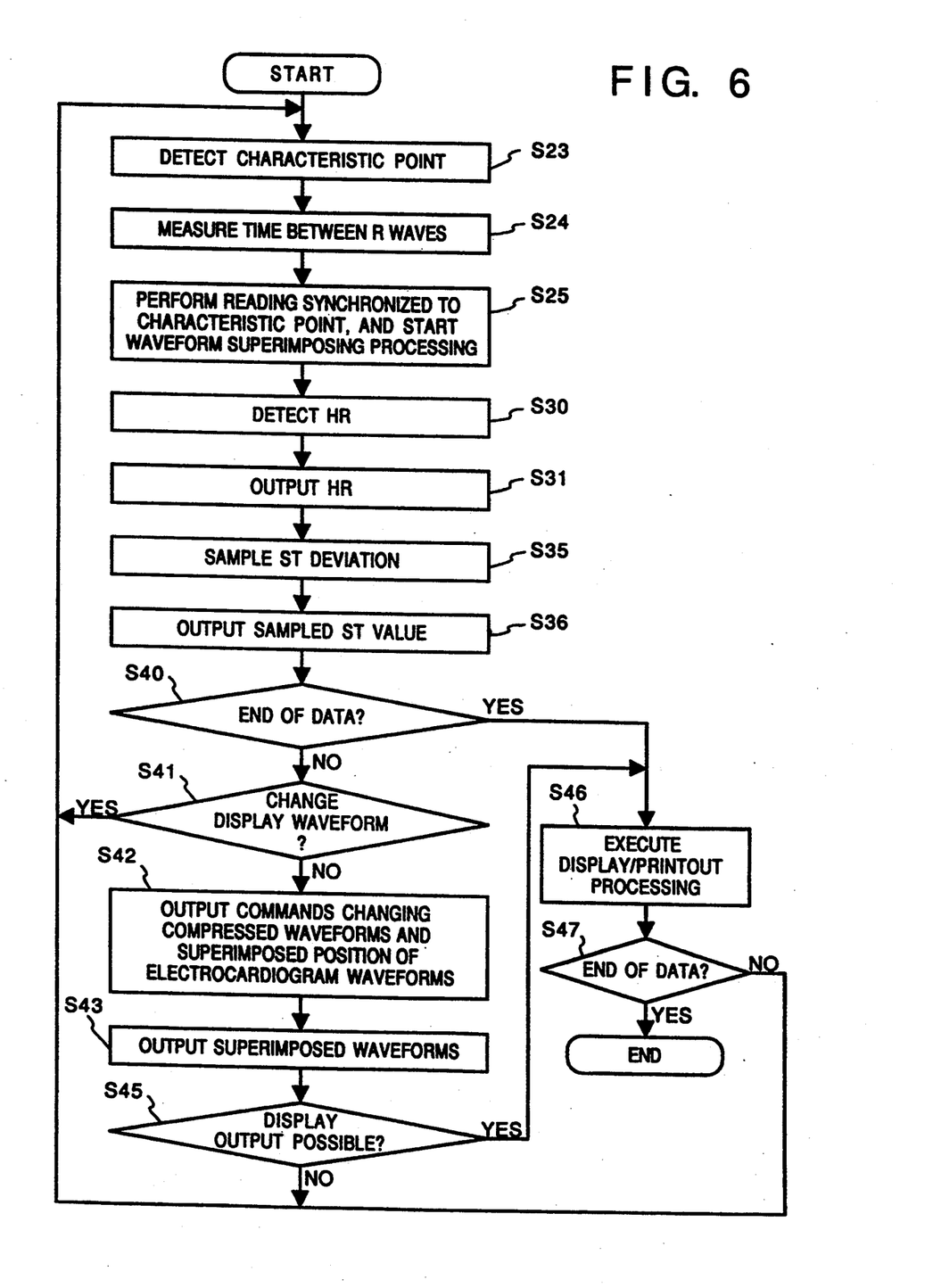

Control for outputting electrocardiograms in the apparatus of this embodiment shown in FIG. 1 will now be described in detail with reference to the flowcharts of FIGS. 4 through 6.

Figure 4:
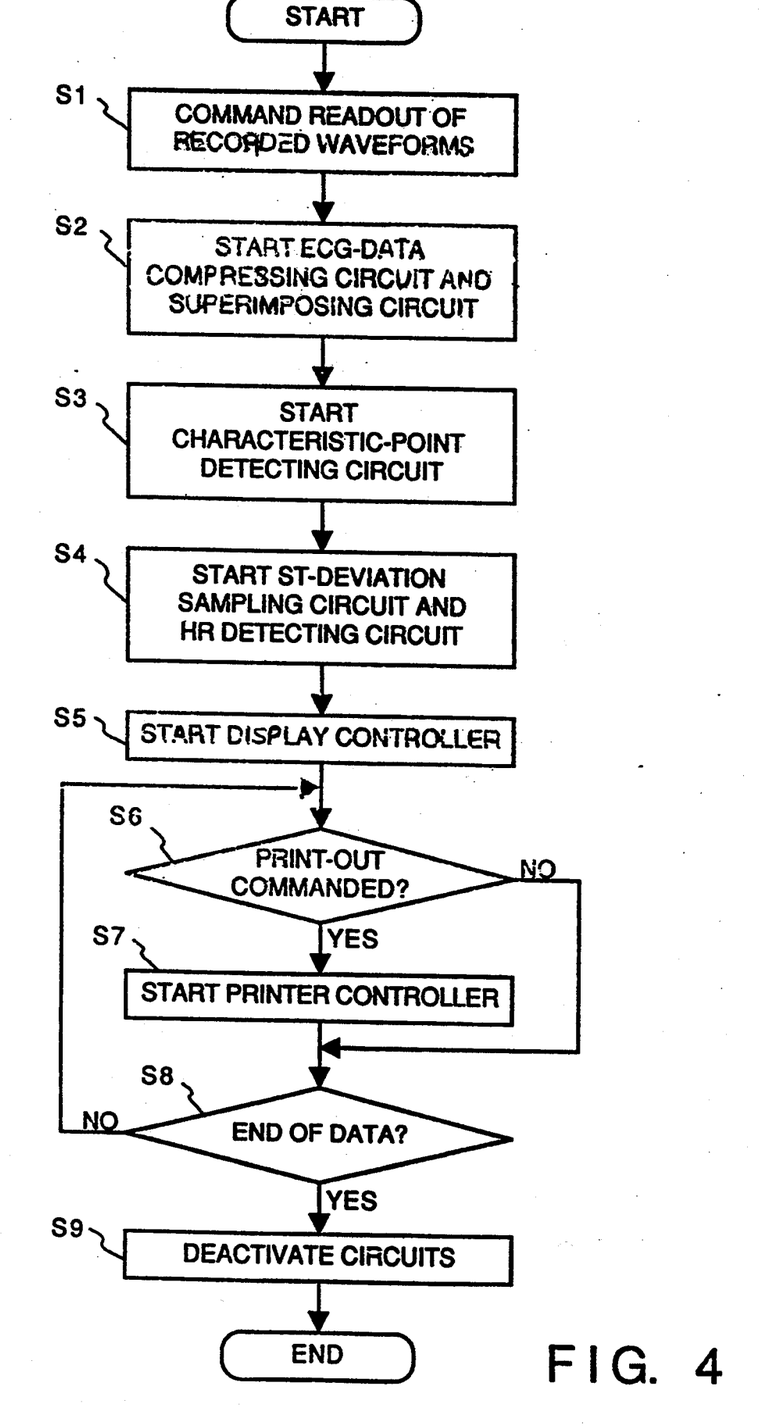
FIGS. 4, 5 and 6 are flowcharts for describing control of electrocardiogram waveform output according to the embodiment.

The cassette tape 30 on which electrocardiogram waveforms have been recorded is loaded in the cassette tape reader 13 of the apparatus and the apparatus is started, whereby the program proceeds to step S1 in FIG. 4. Here the controller 11 instructs the reading circuit 14 to control the cassette tape reader 13 in such a manner that the recorded electrocardiogram waveforms are read out successively and written in the memory 15 at the same time. Preferably, the capacity of memory 15 is sufficient for storage of at least two beats of the electrocardiogram waveforms. In addition, information indicative of the time of the reading operation is set in a timer circuit 24, which is made to perform timekeeping the same as that at the time of recording. This reading processing continues from this point onward.

Next, at step S2, the ECG-data compressing circuit 20 and the superimposing circuit 17 are started, after which the characteristic-point detecting circuit 16 is started at step S3. The ST-deviation sampling circuit 18 and the HR detecting circuit 19 are started at step S4, and then the display controller 25 is started at step S5. Next, it is determined at step S6 whether printing has been commanded or not. If the answer is NO, then the program proceeds to step S8.

If printing has been commanded, on the other hand, the printer controller 22 is started at step S7, after which the program proceeds to step S8. Here it is determined whether the data has ended. The end of data can mean that reading of the electrocardiogram information recorded on the cassette tape 30 has ended or that the end of display/printing processing has been designated by a key or the like, not shown. If the data has not ended, the program returns to step S6. If the data has ended, the circuits started earlier are deactivated and processing is terminated.

When each circuit is started in the foregoing processing, processing assigned to each circuit is executed independently or processing for interrupting the controller 11 is utilized to execute processing circuit by circuit.

Processing for analyzing the electrocardiogram waveforms and a method of generating the compressed waveforms from the electrocardiogram waveforms are described in detail in "Development of Holter Long-Term Electrocardiograms and Automatic Analyzing Apparatus" of the 19th Japan ME Society Convention. Accordingly, a detailed description will not be given here.

An overview of processing for generating compressed electrocardiogram waveforms in the ECG-data compressing circuit 20 is now presented.

The ECG-data compressing circuit 20, which is started at step S11, reads the electrocardiogram waveforms out of the memory at step S12, reads the initially designated electrocardiogram waveforms, compresses the read electrocardiogram waveforms to a predetermined scale by a well-known method and successively stores the compressed waveforms in an internal memory 20a at step S13. It is determined at step S14 whether the generation of one line of compressed waveforms has ended. If the answer is NO, the program proceeds to step S15, at which it is determined whether deactivation has been designated. If the answer is NO, the program returns to step S12. Here, if the measured waveforms are two, e.g., waveforms of channel 1 and waveforms of channel 2, the initially set waveforms are taken as being the measured waveforms of channel 1 at the start.

When one line of compressed electrocardiogram waveforms has been produced, the program proceeds from step S14 to step S16, where the waveforms are sent to the printer controller 22 and the display controller 25. The printer controller 22 and display controller 25 develop control information, which contains the compressed electrocardiogram waveforms, at time-axis positions corresponding to display-output positions of the page buffers 22a, 25a which store a predetermined amount of information. The program then proceeds from step S15 to step S12. If deactivation has been designated at step S15, the program proceeds to step S17, at which the waveforms are sent to the printer controller 22 and the display controller 25. The printer controller 22 and display controller 25 develop control information, which contains the compressed electrocardiogram waveforms, at time-axis positions corresponding to display-output positions of the page buffers 22a, 25a which store a predetermined amount of information. Processing is then terminated.

In the description given above, control is performed in such a manner that the information is written in the page buffers 22a, 25a whenever one line of compressed waveforms is generated. However, it is possible to adopt an arrangement in which the memory 20a is not provided, and in which control would be performed so as to write the information in the page buffers 22a, 25a for every single compressed waveform. It is also possible to exercise control in such a manner that the information is written in the page buffers 22a, 25a every five lines of one waveform.

Control of the superimposing circuit 17, ST-deviation sampling circuit 18 and HR detection circuit 19 will be described with reference to the flowchart of FIG. 6. In FIG. 6, the processing of each circuit is illustrated as being carried out in a time series. In actuality, however, the processing of each circuit is executed independently. In the description that follows, the operation of each circuit is described in the manner of a time series in order to simplify the explanation.

The character-point detecting circuit 16 and the superimposing circuit 17 constantly read out the electrocardiogram waveforms, which have been written in the memory 15, until they are deactivated. The characteristic-point detecting circuit 16 executes processing for detecting the designated characteristic point, namely the peak of the R wave, at step S23. The result of detecting the designated characteristic point is outputted to each circuit. The time from R-wave peak detection of the preceding beat is measured by the HR detection circuit 19 at step S24. This is performed by reading in the timekeeping data from the timer circuit 24.

Next, at step S25, the superimposing circuit 17 reads in the timekeeping data from the timer circuit 24, monitors the passage of time and, in synchronism with the timing of the detection of this characteristic point, superimposes waveforms from the electrocardiogram waveforms whose characteristic point has been detected at a timing the same as that of the previously superimposed waveforms. This is carried out every 30 seconds. Accordingly, the R-wave peaks of these superimposed electrocardiogram waveforms all have the same position. It should be noted that the displaying/recording of the superimposed waveforms is for facilitating the diagnosis of ischemia and the like by allowing observation of the ST deviation. Accordingly, if a waveform is abnormal, sampling is stopped with regard to this abnormal waveform and the next normal electrocardiogram waveform is superimposed. By virtue of the foregoing processing, the superimposing of waveforms inappropriate for diagnosis can be prevented so that more reliable diagnosis is realized.

At step S30, the HR detection circuit 19 calculates the heart rate from the characteristic-point (R-wave peak) detection time interval measured at step S24, and the heart rate is outputted to the display controller 25 and printer controller 22 at the same time as the time information at step S31. The display controller 25 and printer controller 22 develop output information, which contains the HR value, along a time axis corresponding to display-output positions of the page buffers 22a, 25a which store a predetermined amount of information.

Next, at step S35, the ST-deviation sampling circuit 18 is started, it obtains the ST crest value (the crest value from the reference level) of a position a predetermined time after the characteristic point, as mentioned above, and samples this as the ST-deviation value at this position. This is followed by step S36, at which the ST deviation sampling circuit 18 sends its output to the printer controller 22 and display controller 25 at the same time as the time information. The printer controller 22 and display controller 25 develop output information, which contains the ST deviation sampling value, along a time axis corresponding to display-output positions of the page buffers 22a, 25a which store a predetermined amount of information. For example, in this embodiment, as shown at numerals 52 and 53 in FIG. 7, the ST deviation and HR are expressed on the same time axis, in which the time axis is taken as an identical vertical time axis. The ST deviation and HR are taken as locations having different display positions.

Next, at step S40, it is determined whether data has ended (whether data display/print processing has ended). If data has ended, the program proceeds to step S46. If data has not ended, the program proceeds to step S41. Here it is determined whether compression of the electrocardiogram waveforms and superimposition of the waveforms have been carried out for a predetermined period of time. If a predetermined amount (e.g., 10 in five minutes) of waveforms have not been superimposed, the program returns to step S23 and processing for detecting the characteristic point of the next electrocardiogram waveform is executed.

When processing for superimposing a predetermined amount of electrocardiogram waveforms has been executed, the program proceeds from step S41 to step S42, at which time a command to change the compressed and superimposed waveform channel and a command to change the display/recording position of the superimposed waveforms are outputted to the superimposing circuit 17, ECG data compressing circuit 20, printer controller 22 and display controller 25. In response, the superimposing circuit 17 outputs the presently prevailing superimposed waveforms to the display controller 25 and printer controller 22 at step S43 to reset the superimposed waveforms that have been preserved. Further, the display controller 25 and printer controller 22 respond by developing these superimposed waveforms in the page buffers at positions corresponding to the display positions. This is followed by step S45, at which both of the controllers 22, 25 determine whether the data developed in the page buffers is capable of being outputted, i.e., whether one page of output is possible (or whether one line of output is possible). If the data cannot be outputted, the program returns to step S23, where compression processing and superimposition processing for the next electrocardiogram waveform is executed.

If output is found to be possible at step S45, then the program proceeds to step S46. Here one page (one line) of data is displayed on the display unit 26 under the control of the display controller 25, and one page of data is printed out on the printer 23 under the control of the printer controller 22.

When the display and print-out of the data end, the program proceeds to step S47, at which it is determined whether this is the end of the recorded information. If this is not the end of the recorded information, the program returns to step S23 and processing for the next electrocardiogram waveform is executed. If this is the end of the recorded information, on the other hand, processing is terminated.

FIG. 7 illustrates an example of display/output based upon the foregoing processing according to this embodiment. In FIG. 7, an area which is at least two-thirds of the total area is allocated for the output area of the electrocardiogram waveforms. The compressed waveforms are waveforms of channel 1 indicated at numeral 54 and waveforms of channel 2 indicated at numeral 55, in which one minute of each waveform is displayed as one line. The waveforms 54 and the waveforms 55 are displayed alternately every five lines (every five minutes). The superimposed electrocardiogram waveforms superimposed by the superimposing circuit 17 are displayed in an area neighboring the display area of the compressed electrocardiogram waveforms for every channel.

More specifically, as shown in FIG. 7, the superimposed electrocardiogram waveforms corresponding to the compressed waveforms of channel 1 indicated at numeral 54 have a display area equivalent to the number of display lines of the compressed electrocardiogram waveforms of channel 1 on a time axis approximately the same as the display time axis of the compressed waveforms 54. This makes it possible to readily visualize the ST deviation. If the channel of electrocardiogram waveforms to be compressed and outputted changes, the waveforms superimposed also change at the same time and the selected electrocardiogram waveforms to be compressed are adopted for superimposition. For example, when the waveforms of channel 2 are compressed in succession, the superimposed waveforms also become the waveforms of channel 2. The display position also becomes a position, indicated at 57, neighboring the compressed-waveform display position of channel 2.

On a time axis approximately perpendicular to the time axis for output of the compressed waveforms, and with a time corresponding to the compressed-waveform display interval of this line serving as the vertical time axis, an ST-trend graph 52 which displays a change in the ST-crest value at every moment and an HR-trend graph 53 which displays a change in the HR value at every moment are outputted simultaneously.

In accordance with the embodiment described above, long-term compressed electrocardiogram waveforms are outputted, detected R waves are written in superimposed form in synchronism with the R peaks at predetermined time intervals in correlation with the compressed waveforms, and the positions at which writing takes place are shifted whenever the number of displayed lines of compressed electrocardiogram waveforms becomes a fixed number of lines. By combining the ST-trend graph and HR-trend graph of the conventional method with these waveforms and outputting the result, the degree of change in ST and the change in the shape thereof can be recognized with ease.

Second Embodiment

In the embodiment described above, an example is set forth in which R-wave peak is detected as a characteristic point in correlation with compressed electrocardiogram waveforms, the electrocardiogram waveforms at prescribed time intervals or electrocardiogram waveforms which are subjected to an averaging process are superimposed in synchronism with the peak point, and these are displayed as biological information along with HR and ST. However, the characteristic points to be synchronized and the other displayed biological information are not limited to the foregoing. Any biological information may be used so long as it is recorded on a cassette tape.

Further, in the foregoing embodiment, it is described such that the electrocardiogram waveforms are in two channels. However, the number of channels is optional. Output is possible through the same method and approximately the same actions and effects can be obtained even with one channel or three or more channels.

In this embodiment, waveforms are superimposed every 30 seconds. However, the interval of superimposition is arbitrary. This can be every 15 seconds or any other time interval. The same is true for channel changeover time of the electrocardiogram waveforms; any time period can be adopted.

Furthermore, the methods of output and display are not limited to the foregoing.

In accordance with the embodiment, as described above, a predetermined amount of electrocardiogram waveforms are superimposed in synchronization with, say, the P or R waves of the electrocardiogram waveforms, and these are displayed while successively changing the display position. As a result, the waveforms can be displayed in large form in comparison with a case in which all of the waveforms are compressed and displayed within a range decided by the same time axis. Consequently, the shape of the electrocardiogram waveforms can readily be ascertained even up to very fine portions.

Since a large number of waveforms are superimposed, a deviation between waveforms can be recognized very easily. In addition, the ST trend, for example, is taken along the same time axis or a time axis perpendicular thereto along with the superimposed waveforms, and the positions of the superimposed waveforms at a time corresponding to that of the ST-trend waveforms are displayed in a recognizable manner. Consequently, the degree of change in ST can be recognized at a glance, and the change in waveforms is examined by specifying the superimposed waveforms upon observing them, thereby making it possible to recognize a change in a large number of electrocardiogram waveforms quickly and reliably.

Accordingly, the degree of change in electrocardiogram waveform can be distinguished reliably in a short time even in a case where electrocardiogram waveforms from a period of 24 hours are printed out or displayed. A competent diagnosis can be performed by observing the change in waveforms.

In accordance with the present invention, as described above, the ST trend and the compressed waveforms are recorded in correlation. As a result, diagnosis can be carried out with ease. Furthermore, electrocardiogram waveforms which are not compressed also are recorded in correlation with the compressed waveforms at the same time, and therefore the ST deviation can readily be visualized and ischemia can be diagnosed with ease at the same time.

Third Embodiment

In the above embodiments, all electrocardiogram waveforms detected in a predetermined period of time are displayed as compressed waveforms. However, changes in the ST segment of an electrocardiogram waveform needs to be supervised particularly. In the above embodiments, in order to display the whole compressed waveforms, most of the area of a recording paper is reserved for the compressed waveforms, thus resulting in a small space for displaying of the superimposed waveforms, ST trend waveforms, or heart rate trend graph waveforms. In the third embodiment, the above mentioned drawback is improved. A trend indication mode in which only the ST segment from the electrocardiogram waveforms is extracted is provided in the apparatus of the third embodiment.

More particularly, as shown in FIG. 8, an extraction circuit 100 which extracts the ST segment from electrocardiogram waveforms is provided in addition to the apparatus shown in FIG. 1. The extracted waveforms are delivered to the printer controller 22 and display controller 25. The printer controller 22 and the display controller 25 develop the extracted waveforms of the ST segment to the display/output position of the page buffers 22a, 25a which store the output information.

The detail of this processing is described in accordance with the particular electrocardiogram waveforms.

Figure 9A:
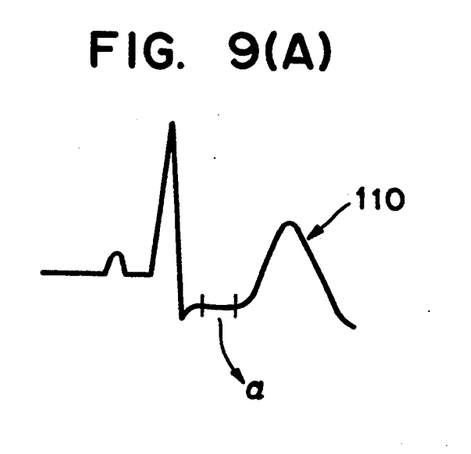
FIG. 9(A) is a diagram explaining an extraction processing of electrocardiograms of the third embodiment.

The extraction circuit 100 extracts the ST segment of the electrocardiogram waveforms 110 denoted by $\alpha$ in FIG. 9(A).

The printer controller 22 and display controller 25 sequentially receive only the extracted waveform $\alpha$ of the ST segment and develop it at a display/output position in the page buffers 22a and 25a. A display area for the ST segment waveform is much smaller than that for the whole compressed electrocardiogram waveforms, resulting in more space in a display layout.

Figure 9B:
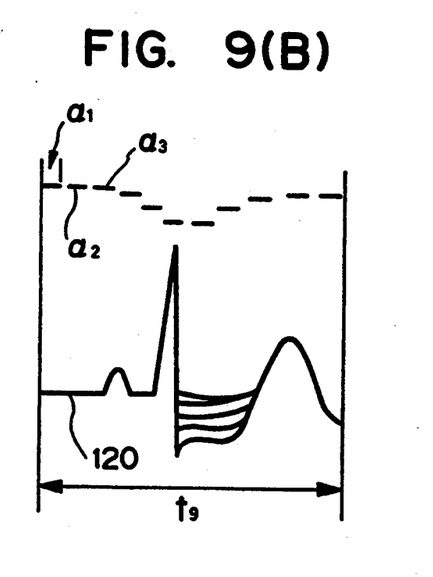
FIG. 9(B) is a diagram showing a display example of the extracted waveform in the third embodiment.

To this end, as shown in FIG. 9(B), the extracted waveform $\alpha$ of the ST segment which is extracted from the waveforms shown in FIG. 9(A) is displayed at the upper side of the display position of the superimposed waveforms 120 while a display position is sequentially changed as $\alpha_1$, $\alpha_2$, $\alpha_3$. It is made possible that the relationship between the superimposed waveform and extracted waveform of the ST segment be clearly distinguished. In FIG. 9(B), the extracted waveform is placed on a time axis in a direction of the width of the superimposed waveform display area. It can be arranged that the extracted waveform of the ST segment of the electrocardiogram waveforms is displayed within the time period $t_9$.

Figure 10:
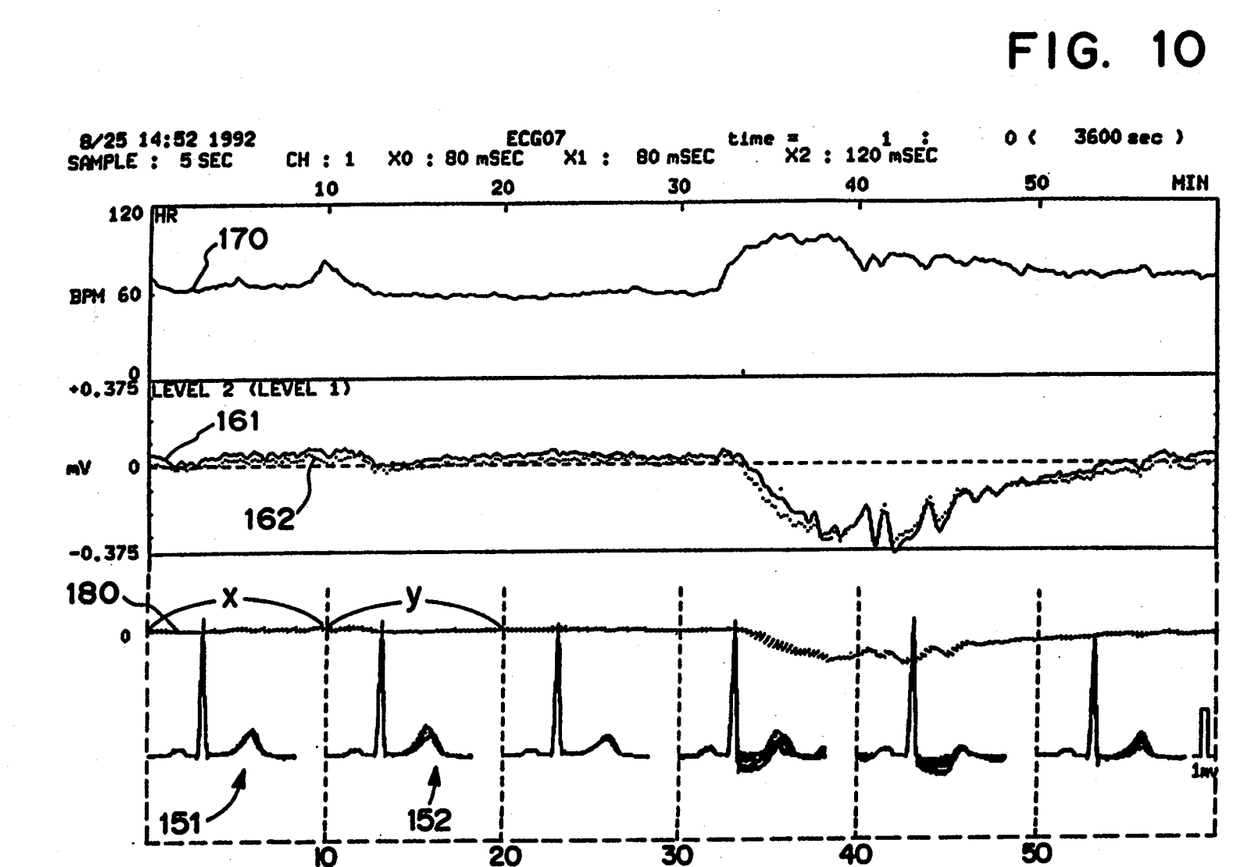
FIG. 10 shows an example of outputs of electrocardiogram waveforms according to the third embodiment.

Accordingly, as shown in FIG. 7, a common time axis can be shared by various items to be displayed without providing a time axis for each display item. For example, the heart rate trend graph, ST level trend graph, extracted waveform of ST segment, and the superimposed electrocardiogram waveforms are displayed along with the time axis. FIG. 10 is an example of the display layout.

In FIG. 10, numeral 151 indicates a superimposed waveform of the electrocardiogram of the channel 1 and numeral 152, a superimposed waveform of the electrocardiogram of the channel 2. Numeral 161 is a trend graph at the ST level of the channel 1, and numeral 162, a trend graph at the ST level of the channel 2. In FIG. 10, both trend graphs can be easily distinguished. Providing a color can be also arranged for each channel so that each trend graph is easily distinguished.

Numeral 180 is a heart rate trend graph displaying the ST segment waveform. In FIG. 10, the ST segment waveform of a channel of the superimposed waveforms is displayed at the upper side of the superimposed waveform display. However, this does not impose a limitation upon the present invention. It can be arranged so as to display all waveforms in the ST segment for every channel by dividing the display area into, e.g. two levels.

As many apparently widely different embodiments of the present invention can be made without departing from the spirit and scope thereof, it is to be understood that the invention is not limited to the specific embodiments thereof except as defined in the appended claims.

What is claimed is:

1. Apparatus for recording electrocardiogram information, comprising:
   means for reading electrocardiogram waveforms and outputting in binary form;
   memory means for storing the binary form of said electrocardiogram waveforms from said reading and outputting means;
   means for compressing said electrocardiogram waveforms into compressed waveforms, said compressing means reading the binary form of said waveforms from said memory means;
   a recording medium having first, second, and third areas;
   means for recording said compressed waveforms as a plurality of first lines in the first area of said recording medium;
   means for detecting a characteristic point common to said electrocardiogram waveforms, said detecting means reading the binary form of said electrocardiogram waveforms from said memory means;
   means for creating analyzed results based on said electrocardiogram waveforms read by said detecting means, said recording means recording said analyzed results along second lines approximately perpendicular to the first lines for compressed waveforms recorded in the first area, said second lines being recorded in the second area of the recording medium;
   means for selecting a first predetermined number of said electrocardiogram waveforms from a second predetermined number of said lines in the first area of said recording medium and superimposing the selected waveforms in synchronism with the characteristic point of the selected waveforms, said recording means recording the superimposed waveforms in the third area of the recording medium while changing location in the third area for every second predetermined number of lines of the first recording area; and
   preprogrammed means for controlling said reading means, said memory means, said compressing means, said detecting means, said creating means, and said selecting and superimposing means.

2. Apparatus in accordance with claim 1 wherein said reading and outputting means includes a cassette tape reader, a cassette tape having electrocardiogram waveforms recorded thereon, and a circuit which controls in combination with said controlling means the cassette tape reader, binarizes the waveforms, and outputs the binary form of the waveforms to said memory means.

3. Apparatus in accordance with claim 2 wherein said controlling means includes timing means for sensing electrocardiogram waveform rate when the electrocardiogram waveforms were recorded on said cassette tape and for controlling use of said rate.

4. Apparatus in accordance with claim 1 wherein said recording medium is paper.

5. Apparatus in accordance with claim 4 wherein said recording means includes a printer and printer control means for controlling said printer, said recording means further including a page buffer for providing memory in which print information for the first, second, and third areas equivalent to one page when printed on said paper is developed, said one page being outputted through said printer control means for printing on said paper by said printer when development of the one page of print information ends.

6. Apparatus in accordance with claim 1 wherein said recording medium is a CRT display screen.

7. Apparatus in accordance with claim 6 wherein said recording means includes means for controlling said CRT display, said recording means further including a page buffer for providing memory in which display information for the first, second, and third areas equivalent to one page for display on the screen is developed, said one page being outputted through said controlling means for display on said CRT display screen when development of the one page of display information ends.

8. Apparatus in accordance with claim 1 wherein said analyzed results creating means includes an ST-deviation sampling circuit for obtaining ST trend and an HR detecting circuit for obtaining heart rate.

9. Apparatus in accordance with claim 1 including a plurality of channels of information input to said recording means, each of said channels including reading means, memory means, compressing means, detecting means, creating means, and selecting and superimposing means, said recording means recording alternately a set of a predetermined number of said first lines in the first area for each of said channels, said set having a width extending across the predetermined number of first lines, said recording means recording the superimposed waveforms for each of said sets of predetermined lines for each channel in a subarea of the second area such that the subarea has a height equal to the width extending across the predetermined number of first lines.

10. Apparatus in accordance with claim 1 wherein the compressed waveforms of said first recording area are such that one minute of time corresponds to one line.

11. Apparatus in accordance with claim 1 wherein the predetermined characteristic point of the selected waveforms is an R-wave peak.

12. A method for recording electrocardiogram information, comprising the steps of:
reading with a first circuit information on electrocardiogram waveforms and storing the information in memory means;
compressing said electrocardiogram waveforms into compressed waveforms with a data compressing second circuit;
analyzing with a third circuit said information to obtain analyzed results;
selecting with a fourth circuit a first predetermined number of electrocardiogram waveforms as selected waveforms and superimposing the selected waveforms in synchronism with a characteristic point of the selected waveforms to create superimposed waveforms;
recording with controlling means said compressed waveforms as a plurality of first lines in a first area of a recording medium;
recording with said controlling means said analyzed results along second lines approximately perpendicular to the first lines for compressed waveforms recorded in the first area, said second lines being recorded in a second area of the recording medium; and
recording with said controlling means said superimposed waveforms in a third area of the recording medium while changing location in the third area for every predetermined number of first lines of the first recording area.

13. The method in accordance with claim 12 wherein the reading step includes the steps of receiving from a cassette tape recorder information on electrocardiogram waveforms as recorded on a cassette tape and converting the information to binary form.

14. The method in accordance with claim 13 wherein said reading step includes the step of sensing electrocardiogram waveform rate when the electrocardiogram waveforms were recorded on said cassette tape.

15. The method in accordance with claim 12 wherein said analyzing step and said selecting and superimposing step include detecting a characteristic point common to said electrocardiogram waveforms.

16. The method in accordance with claim 12 wherein said recording steps include storing in a memory buffer information for one page to be recorded in the first, second, and third areas of the recording medium.

17. The method in accordance with claim 16 wherein said recording steps further include printing with a printer said one page of information on paper.

* * * * *